United States Patent [19]

Jeschke et al.

[11] Patent Number: 5,585,493
[45] Date of Patent: Dec. 17, 1996

[54] USE OF SUBSTITUTED 1,2,4-OXADIAZOLE DERIVATIVES FOR COMBATING ENDOPARASITES, NEW SUBSTITUTED 1,2,4-OXADIAZOLE DERIVATIVES, AND PROCESSES FOR THEIR PREPARATION

[75] Inventors: Peter Jeschke, Leverkusen; Werner Lindner; Achim Harder, both of Cologne; Norbert Mencke, Leverkusen; Axel Haberkorn, Wuppertal, all of Germany

[73] Assignee: Bayer Aktiengesellschaft, Leverkusen, Germany

[21] Appl. No.: 288,173

[22] Filed: Aug. 10, 1994

Related U.S. Application Data

[62] Division of Ser. No. 57,584, May 5, 1993, Pat. No. 5,371,231, which is a continuation of Ser. No. 800,334, Nov. 27, 1991, abandoned.

[30] Foreign Application Priority Data

Dec. 22, 1990 [DE] Germany .......... 40 414 74.4

[51] Int. Cl.⁶ .......................... C07D 271/06
[52] U.S. Cl. .......................... 548/131
[58] Field of Search .......................... 548/131

[56] References Cited

U.S. PATENT DOCUMENTS 4,012,377  3/1977  Claisse .................. 548/131

FOREIGN PATENT DOCUMENTS 1357733  6/1974  United Kingdom .

OTHER PUBLICATIONS

Yale, J. Het Chem. 15 1373 (1978).

Claisse II, J. Chem Soc. Perkins (20) 2241 (1973).

Journal of the Chemical Society, Perkin Transactions 1, 1973, London GB, pp. 2241–2249, J. A. Claisse et al.

*Primary Examiner*—Robert Gerstl
*Attorney, Agent, or Firm*—Sprung Horn Kramer & Woods

[57] ABSTRACT

Substituted 1,2,4-oxadiazole derivatives of the formula (I) and their stereoisomers

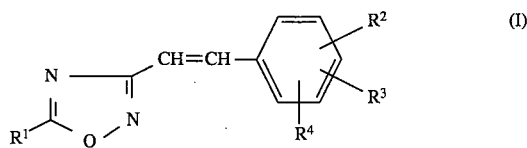

in which formula $R^1$ represents hydrogen, $C_{1-8}$-alkyl which is optionally substituted by halogen, cycloalkyl, alkoxy, hydroxyl, aryl, alkylcarbonyl, alkoxycarbonyl and cycloalkyl, and their use as endoparasiticides.

4 Claims, No Drawings

USE OF SUBSTITUTED 1,2,4-OXADIAZOLE DERIVATIVES FOR COMBATING ENDOPARASITES, NEW SUBSTITUTED 1,2,4-OXADIAZOLE DERIVATIVES, AND PROCESSES FOR THEIR PREPARATION

This application is a divisional of application Ser. No. 08/057,584, filed on May 5, 1993, now U.S. Pat. No. 5,371,231, which is a continuation of Ser. No. 07/800,334, filed on Nov. 27, 1991, now abandoned.

The present invention relates to new substituted 1,2,4-oxadiazole derivatives, processes for their preparation, and their use as endoparasiticides.

It has already been disclosed that certain 1,2,4-oxadiazoles such as, for example, the compound (E)-3-styryl-1,2,4-oxadiazole have parasiticidal activity (cf., for example, U.S. Pat. No. 4,012,377). However, the activity of these previously known compounds is not entirely satisfactory when low amounts and concentrations are applied.

The present invention relates to the following:

1. New substituted 1,2,4-oxadiazole derivatives of the general formula (I) and their stereoisomers $$\text{(I)}$$

in which formula $R^1$ represents hydrogen, $C_{1-8}$-alkyl which is optionally substituted by halogen, cycloalkyl, alkoxy, hydroxyl, aryl, alkylcarbonyl, alkoxycarbonyl and cycloalkyl, $R^2$ represents hydrogen, halogen, $NO_2$, CN, alkyl, halogenoalkyl, alkoxy or thioalkyl, $R^3$ represents hydrogen, halogen, $NO_2$, CN, alkyl, halogenoalkyl, alkoxy or thioalkyl, $R^4$ represents OH, SH, halogenoalkoxy, halogenoalkylthio, halogenoalkylsulphinyl, halogenoalkylsulphonyl, aryloxy, aralkoxy, arylthio, aralkylthio, alkylenedioxy, halogenoalkylene dioxy, amino, alkylamino, dialkylamino, acylamino, carbamoyl, alkylsulphinyl, alkylsulphonyl, arylsulphinyl, arylsulphonyl, sulphonylamino, alkoxycarbonyl, alkylcarbonyl, alkylcarbonyloxy, alkoxyalkyl, alkoxyalkoxy or hydroxyalkoxy, where, in the event that at least one of the radicals $R^2$ or $R^3$ is other than hydrogen, $R^4$ additionally represents halogen, alkyl, halogenoalkyl, alkoxy or thioalkyl, where, in the event that $R^1$ represents optionally substituted $C_{1-8}$-alkyl, $R^4$ additionally represents alkoxy.

2. Processes for the preparation of the substituted 1,2,4-oxadiazole derivatives of the formula (I) and their stereoisomers $$\text{(I)}$$

in which formula $R^1$ represents hydrogen, $C_{1-8}$-alkyl which is optionally substituted by halogen, cycloalkyl, alkoxy, hydroxyl, aryl, alkylcarbonyl, alkoxycarbonyl and cycloalkyl, $R^2$ represents hydrogen, halogen, $NO_2$, CN, alkyl, halogenoalkyl, alkoxy or thioalkyl, $R^3$ represents hydrogen, halogen, $NO_2$, CN, alkyl, halogenoalkyl, alkoxy or thioalkyl, $R^4$ represents OH, SH, halogenoalkoxy, halogenoalkylthio, halogenoalkylsulphinyl, halogenoalkylsulphonyl, aryloxy, aralkoxy, arylthio, aralkylthio, alkylenedioxy, halogenoalkylenedioxy, amino, alkylamino, dialkylamino, acylamino, carbamoyl, alkylsulphinyl, alkylsulphonyl, arylsulphinyl, arylsulphonyl, sulphonylamino, alkoxycarbonyl, alkylcarbonyl, alkylcarbonyloxy, alkoxyalkyl, alkoxyalkoxy or hydroxyalkoxy, where, in the event that at least one of the radicals $R^2$ or $R^3$ is other than hydrogen, $R^4$ additionally represents halogen, alkyl, halogenoalkyl, alkoxy or thioalkyl, where, in the event that $R^1$ represents optionally substituted $C_{1-8}$-alkyl, $R^4$ additionally represents alkoxy, characterised in that an amide oxime derivative of the formula (II) and stereoisomers thereof $$\text{(II)}$$

in which formula $R^2$, $R^3$ and $R^4$ have the abovementioned meanings, a) are reacted with a carboxylic acid orthoester of the formula (III)

$$R^1\text{—C(O—A)}_3 \qquad \text{(III)}$$

in which $R^1$ has the abovementioned meaning and

A represents alkyl, in particular methyl or ethyl, or b) are reacted with a carboxylic acid ester of the formula (IV)

$$\text{(IV)}$$

in which $R^1$ and A have the abovementioned meaning or c) are reacted with carboxylic anhydrides of the formula (V)

$$(R^1\text{—CO})_2\text{O} \qquad \text{(V)}$$

in which $R^1$ has the abovementioned meaning or d) are reacted with a carboxylic acid halide of the formula (VI)

$$\text{(VI)}$$

in which $R^1$ has the abovementioned meaning and

Hal represents halogen, such as fluorine, chlorine or bromine, preferably chlorine, in the presence of a diluent and in the presence of a reaction auxiliary.

The compounds Of the formula (I) are outstandingly suitable for use as endoparasiticides, in particular in the field of veterinary medicine.

Surprisingly, the substituted 1,2,4-oxadiazole derivatives of the general formula (I) according to the invention show a considerably better activity against endoparasites than the 1,2,4-oxadiazoles which are known from the prior art, such as, for example, the compound (E)-3-styryl-1,2,4-oxadiazole or (E)-3-(4-chloro-styryl)-1,2,4-oxadiazole, which are similar compounds as regards their structure and activity (cf., for example, U.S. Pat. No. 4,012,377).

Formula (I) provides a general definition of the substituted 1,2,4-oxadiazole derivatives according to the invention.

Preferred compounds of the formula (I) ere those in which $R^1$ represents hydrogen, $C_{1-6}$-alkyl which is optionally substituted by 1 to 6 halogen atoms such as fluorine or chlorine, $C_{3-6}$-cycloalkyl, $C_{1-6}$-alkoxy, hydroxyl, optionally substituted phenyl, $C_{1-4}$-alkylcarbonyl, $C_{1-6}$-alkoxycarbonyl and $C_{3-6}$-cycloalkyl, in particular cyclopropyl, cyclopentyl or cyclohexyl, $R^2$ represents hydrogen, halogen, in particular fluorine, chlorine or bromine, CN, $NO_2$, $C_{1-6}$-alkyl, 1 to 6 halogeno-$C_{1-6}$-alkyl, in particular triflouromethyl, trichloromethyl or fluoro-chloroethylene, $C_{1-6}$-alkoxy, in particular methoxy, ethoxy or isopropoxy or $C_{1-6}$-thioalkyl, in particular methylthio, $R^3$ represents one of the radicals mentioned in the case of $R^2$, $R^4$ represents OH, SH, 1 to 5 halogeno-$C_{1-6}$-alkoxy, 1 to 6 halogeno-$C_{1-4}$-alkylthio, 1 to 6 halogeno-$C_{1-6}$-alkylsulphinyl, 1 to 5 halogeno-$C_{1-6}$-alkylsulphonyl, optionally substituted phenoxy, optionally substituted phenylmercapto, optionally substituted phenyl-$C_{1-6}$alkoxy, optionally substituted phenyl-$C_{1-6}$-alkylthio, $C_{1-2}$-alkylenedioxy, 1 to 4 halogeno-$C_{1-2}$-alkylenedioxy, amino, $C_{1-6}$-alkylamino, di-$C_{1-4}$-alkylamino, acylamino such as, in particular, acetylamino, or benzenesulphonylamino, carbamoyl such as, in particular, the radicals —$CONH_2$, —$CONH(C_{1-4}$-alkyl), or $C_{1-4}$-alkylsulphinyl, $C_{1-4}$-alkylsulphonyl, sulphonylamino such as, in particular, the radicals —$SO_2NH_2$, —$SO_2NH$ ($C_{1-4}$-alkyl), or $C_{1-4}$-alkoxycarbonyl, $C_{1-4}$-alkylcarbonyl, $C_{1-4}$-alkylcarbonyloxy, $C_{1-4}$-alkoxy-$C_{1-4}$-alkyl, $C_{1-4}$-alkyl-$C_{1-4}$-alkoxy and hydroxy-$C_{1-4}$-alkoxy, and, in the event that at least one of the radicals $R^2$ and $R^3$ is other than hydrogen, additionally represents halogen such as fluorine, chlorine or bromine, $C_{1-4}$-alkyl, 1 to 6 halogeno-$C_{1-4}$-alkyl, 1 to 6 halogeno-$C_{1-4}$-alkyl, $C_{1-4}$-alkoxy or $C_{1-4}$-alkylthio.

The following may be mentioned as possible substituents of the optionally substituted radicals: halogen, in particular fluorine, chlorine or bromine, $C_{1-4}$-alkyl, in particular methyl, $C_1$-$C_4$-halogenoalkyl, in particular trifluoromethyl, $C_1$-$C_4$-alkoxy, in particular methoxy, isopropyloxy, $C_1$-$C_4$-halogenoalkoxy, in particular trifluoromethoxy, difluoromethoxy, fluorochloroethoxy, hexafluoropropyloxy, $C_1$-$C_4$-halogenoalkylthio, in particular trifluoromethylthio, fluorochloromethylthio, $C_1$-$C_4$-halogenoalkylsulphinyl, in particular trifluoromethylsulphinyl, $C_1$-$C_4$-halogenoalkylsulphonyl, in particular trifluoromethylsulphonyl, methylenedioxy or ethylenedioxy, which are optionally substituted by fluorine or chlorine, or amino, $C_1$-$C_4$-alkyl- and dialkylamino, or acylamino, in particular acetylamino.

Very particularly preferred compounds of the formula (I) are those in which $R^1$ represents hydrogen: $C_{1-6}$-alkyl optionally substituted by 1 to 6 halogen atoms such as fluorine or chlorine, $C_{3-6}$-cycloalkyl, $C_{1-6}$-alkoxy, hydroxyl, optionally substituted phenyl, $C_{1-4}$-alkylcarbonyl, $C_{1-6}$-alkoxycarbonyl and also represents $C_{3-6}$-cycloalkyl, in particularly cyclopropyl, cyclopentyl or cyclohexyl, $R^2$ represents hydrogen, halogen, in particular fluorine, chlorine or bromine, CN, $NO_2$, $C_{1-6}$-alkyl, 1 to 6 halogeno-$C_{1-6}$-alkyl, in particular trifluoromethyl, trichloromethyl or fluoro-chloroethylene, $C_{1-6}$-alkoxy, in particular methoxy, ethoxy or isopropoxy, or $C_{1-6}$-thioalkyl, in particular methylthioalkyl, in particular methylthio, $R^3$ represents halogen, in particular fluorine, chlorine or bromine, CN, $NO_2$, $C_{1-6}$-alkyl, 1 to 6 halogeno-$C_{1-6}$-alkyl, in particular trifluoromethyl, trichloromethyl or fluoro-chloroethylene, $C_{1-6}$-alkoxy, in particular methoxy, ethoxy or isopropoxy or $C_{1-6}$-thioalkyl, in particular methylthio, $R^4$ represents OH, SH, 1 to 5 halogeno-$C_{1-6}$-alkoxy, 1 to 5 halogeno-$C_{1-4}$-alkylthio, 1 to 6 halogeno-$C_{1-6}$-alkylsulphinyl, 1 to 5 halogeno-$C_{1-6}$-alkylsulphonyl, optionally substituted phenoxy, optionally substituted phenylmercapto, optionally substituted phenyl-$C_{1-6}$-alkoxy, optionally substituted phenyl-$C_{1-6}$-alkylthio, $C_{1-2}$-alkylenedioxy, 1 to 4 halogeno-$C_{1-2}$-alkylenedioxy, amino, $C_{1-6}$-alkylamino, di-$C_{1-4}$-alkylamino, acylamino such as, in particular, acetylamino, or benzenesulphonylamino, carbamoyl such as, in particular, the radicals —$CONH_2$, —$CONH(C_{1-4}$-alkyl), or $C_{1-4}$alkylsulphinyl, $C_{1-4}$-alkylsulphonyl: sulphonylamino such as, in particular: the radicals —$SO_2NH_2$, —$SO_2NH$ ($C_{1-4}$-alkyl), or $C_{1-4}$-alkoxycarbonyl, $C_{1-4}$-alkylcarbonyl, $C_{1-4}$-alkoxycarbonyloxy, $C_{1-4}$-alkoxy-$C_{1-4}$-alkyl, $C_{1-4}$-alkoxy and hydroxy-$C_{1-4}$-alkoxy, and additionally represents halogen such as fluorine, chlorine or bromine, $C_{1-4}$-alkyl, 1 to 6 halogeno-$C_{1-4}$-alkyl, $C_{1-4}$-alkoxy or $C_{1-4}$-alkylthio.

Particular mention may be made of compounds of the formula (I), in which $R^1$ has the abovementioned meaning, $R^2$ represents hydrogen, $R^3$ represents fluorine or chlorine and $R^4$ represents fluorine or chlorine.

Furthermore, particular mention may be made of compounds of the formula (I), in which $R^1$, represents optionally substituted alkyl $R^2$ and $R^3$ have the abovementioned meaning, $R^4$ represents $C_{1-4}$-alkoxy, in particular methoxy.

The following compounds (I) in which the radicals $R^1$ $R^2$, $R^3$ and $R^4$ have the meaning indicated, may be mentioned individually.

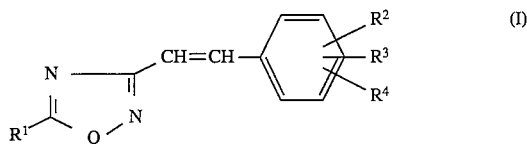

| $R^1$ | $R^2$ | $R^3$ | $R^4$ |
|---|---|---|---|
| —Et | —H | 2-F | 3-Cl |
| △ | —H | 2-F | 3-Cl |
| ⬡ | —H | 2-F | 3-Cl |

-continued

| R¹ | R² | R³ | R⁴ |
|---|---|---|---|
| -iPr | -H | 2-Cl | 3-Cl |
| -CF₃ | -H | 2-Cl | 3-Cl |
| -CCl₃ | -H | 2-F | 3-F |
| -CF₃ | -H | 3-Cl | 4-Cl |
| -CF₂Cl | -H | 3-Cl | 4-Cl |
| -CF₂-CF₃ | -H | 3-Cl | 4-Cl |
| -H | -H | | 2,3-O-CF₂-O- |
| -H | -H | | 2,3-O-CF₂-CH-O- |
| | | |            F |
| -H | -H | 2-CH₃ | 3-CF₃ |
| -H | 2-F | 3-Cl | 4-F |
| -H | 2-F | 3-Cl | 4-CF₃ |
| -H | 2-Cl | 3-CF₃ | 6-Cl |
| -H | 2-Cl | 3-Cl | 4-CF₃ |
| -H | 2-F | 3-CF₃ | 4-F |
| -Me | -H | 3-CH₃ | 4-OCH₃ |
| -H | -H | 2-CH₃ | 3-CH₃ |
| -H | -H | 3-OCH₃ | 4-OCH₃ |
| -H | -H | 2-CH₃ | 4-N(CH₃)₂ |
| -H | -H | 2-CH₃ | 4-Phenyl |
| -H | -H | 3-Br | 4-Cl |
| -H | 3-OCH₃ | 4-OCH₃ | 5-OCH₃ |

The compounds of the formula (I) are new, and they can be prepared by processes a) to d) indicated above under 2) (cf., for example, U.S. Pat. No. 4,012,377; Claisse et al. J. Chem. Soc. Perkin, Trans. I, 20 (1973), p. 241 to 2249).

If, in processes 2a) for the preparation of the new substituted 1,2,4-oxadiazole derivatives, (E)-4-chloro-3-trifluoromethyl-cinnemamide oxide is employed as compounds of the formula (II) and triethyl orthoformate as compound of the formula (III), the process can be illustrated by the following equation.

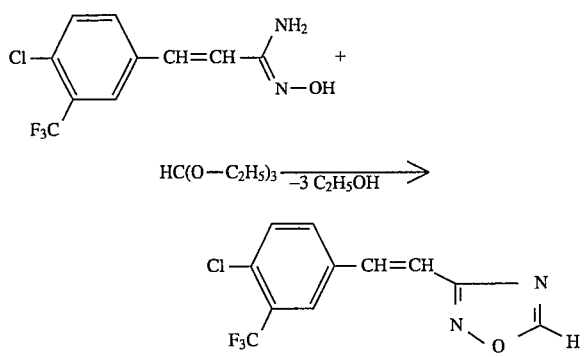

Formula (II) provides a general definition of the amide oximes required as starting materials for carrying out process 2a) according to the invention. In this formula, R², R³ and R⁴ preferably represent those radicals which have already been mentioned in connection with the description of the substances of the formula (I) according to the invention as being preferred for these substituents.

Some of the compounds of the formula (II) which are used as starting materials are known (cf., for example, Claisse et al. J. Chem. Soc. Perkin, Trans. I 20 (1973), p. 2241 to 2249; Yale et al. J. Heterocycl. Chem. 15(8), p. 1373 to 1378) or can be obtained by the processes described therein.

The compounds of the formula (II) can exist in the form of geometric isomers or mixtures of isomers of various composition.

The carboxylic acid orthoesters of the formula (III) which are furthermore to be used on starting substances for carrying out process 2a) according to the invention are generally defined. In this formula (III), R¹ has the meaning which have already been mentioned in connection with the description of the substances of the formula (I) according to the invention as being preferred for this substituent. The carboxylic acid orthoesters of the formula (III) are generally known compounds of organic chemistry.

The following compounds of the formula (II) may be mentioned individually:

$$H_2N\diagdown C(=N-OH)-CH=CH-\text{Aryl}(R^2,R^3,R^4) \quad (II)$$

| R² | R³ | R⁴ | R² | R³ | R⁴ |
|---|---|---|---|---|---|
| -H | 2-Cl | 3-Cl | -H | | 3,4-O-CH₂-O- |
| -H | 2-NO₂ | 4-CF₃ | -H | | 3,4-O-(CH₂)₂-O- |
| -H | 2-F | 6-Cl | -H | | 3,4-O-CF₂-O- |
| -H | 2-CH₃ | 3-Cl | -H | -H | 4-SCF₃ |
| -H | 2-F | 6-F | -H | -H | 4-OCF₃ |
| -H | 2-Cl | 6-Cl | -H | 3-F | 4-F |
| -H | 2-Cl | 3-F | -H | 4-Cl | 3-CF₃ |
| -H | 2-F | 3-CF₃ | -H | -H | 4-(O-CH₂-C₆H₄-Cl) |
| -H | 2-Cl | 3-CF₃ | -H | -H | 4-(O-CH₂-(2,4-Cl₂-C₆H₃)) |

The compounds of the formula (II) and (III) are preferably reacted in the presence of an acid catalyst. Suitable catalysts for this purpose are virtually all mineral acids or Lewis acids. The mineral acids preferably include hydrohalic acids such as hydrofluoric acid, hydrochloric acid, hydrobromic acid or hydroiodic acid, and also sulphuric acid, phosphoric acid, phosphorous acid and nitric acid, and the Lewis acids preferably include aluminium chloride, boron trifluoride or its etherate, titanium(IV) chloride and tin(IV) chloride.

The following Lewis acids are particularly preferably employed:

boron trifluoride or its etherate, and aluminium chloride.

Process 2a) is carried out by combining compounds of the formula (II) with an excess of the compounds of the formula (III) and heating the mixture in the presence of an acid catalyst. In this context, the compound (III) is simultaneously the diluent. The duration of the reaction is approximately 1 to 4 hours. The reaction is carried out at temperatures between +20° C. and +200° C., preferably between +100° C. and +155° C. The process is preferably carried out at the pressure which is generated under the reaction conditions when the mixture is heated to the reaction temperature required.

When the reaction is complete, the reaction mixture is cooled and concentrated in vacuo, and the residue which remains is taken up in an organic solvent and worked up in a manner known per se. The products obtained can be purified in the customary manner by recrystallisation, distillation in vacuo, or column chromatography (cf. also the Preparation Examples).

Alternatively, this reaction can also be carried out using a Meerwein reagent (for example a dialkyl acetal of dimethylformamide) or the Vilsmeier-Haack reagent (POCl₃, N,N-dimethylformamide).

If, in process 2b), (E)-3-chloro-2-fluoro-cinnamamide oxide is employed as compound of the formula (II) and ethyl acetoacetate as compound of the formula (IV), the process can be described by the following equation:

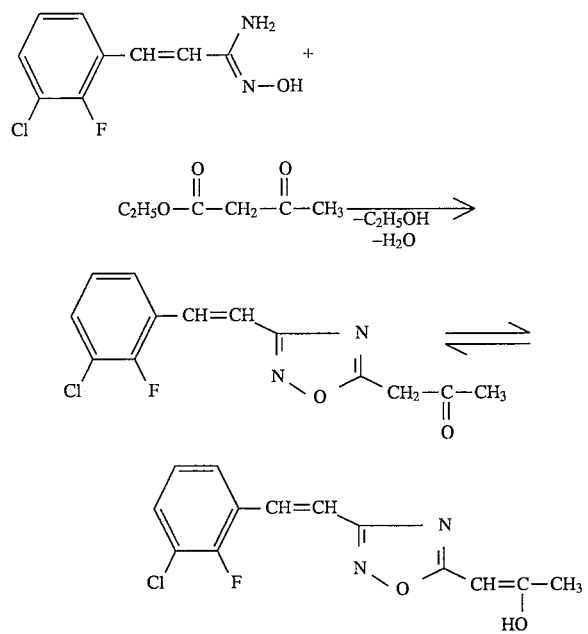

The compounds of the formula (I) can exist in the form of their various tautomers (keto/enol) as well as as a mixture of these tautomers of various composition.

It is preferred to employ the compounds of the formula (II) in process 2b) in which the radicals $R^2$, $R^3$ and $R^4$ have the preferred and the particularly preferred meanings mentioned in the case of the compounds of the formula (I). The carboxylic acid esters (IV) which are furthermore to be used on starting substances for carrying out process 2b) according to the invention are generally defined. The carboxylic acid esters of the formula (IV) are generally known compounds of organic chemistry.

The reaction is preferably carried out using diluents. Suitable diluents for carrying out process 2b) according to the invention are all inert organic solvents.

The following may be mentioned as examples: halogenohydrocarbons, in particular chlorohydrocarbons such as tetrachloroethylene, tetrachloroethane, dichloropropane, methylene chloride, dichlorobutane, chloroform, carbon tetrachloride, trichtoroethane, trichloroethylene, pentachloroethane, difluorobenzene, 1,2-dichloroethane, chlorobenzene, dichlorobenzene, chlorotoluene, trichlorobenzene; ethers such as ethyl propyl ether, methyl tert.butyl ether, n-butyl ethyl ether, di-n-butyl ether, diisobutyl ether, diisoamyl ether, diisopropyl ether, anisole, phenetole, cyclohexyl methyl ether, diethyl ether, ethylene glycol dimethyl ether, tetrahydrofuran, dioxane, dichlorodiethyl ether; nitrohydrocarbons such as nitromethane, nitroethane, nitrobenzene, chloronitrobenzene, o-nitrotoluene; nitriles such as acetonitrile, butyronitrile, isobutyronitrile, benzonitrile, m-chtorobenzonitrile; aliphatic, cycloaliphatic or aromatic hydrocarbons such as heptane, hexane, nonane, cymene, benzine fractions within a boiling point interval from 70° C. to 190° C., cyclohexane, methylcyclohexane, petroleum ether, ligroin, octane, benzene, toluene, xylene; esters such as ethyl acetate, isobutyl acetate; amides for example formamide, N-methylformamide, N,N-dimethylformamide, N-methylpyrrolidone; ketones such as acetone or methyl ethyl ketone. Mixtures of the solvents and diluents mentioned are also suitable.

Aromatic hydrocarbons are preferred.

Process 2b) is carried out by combining compounds of the formula (II) with an excess of the compounds of the formula (IV) in one of the diluents mentioned and heating the mixture. The duration of the reaction is 10 to 80 hours. When the reaction is complete, the mixture is cooled and concentrated in vacuo, and the solid obtained is filtered off, washed and dried.

The reaction is carried out at temperatures between +50° C. and +160° C., preferably at temperatures between +80° C. and 110° C. The process is carried out under atmospheric pressure.

If, in process 2c), (E)-2,3-dichloro-cinnamamide oxime is employed as compound of the formula (II) and acetic anhydride is employed as compounds of the formula (V), the process can be illustrated by the following equation:

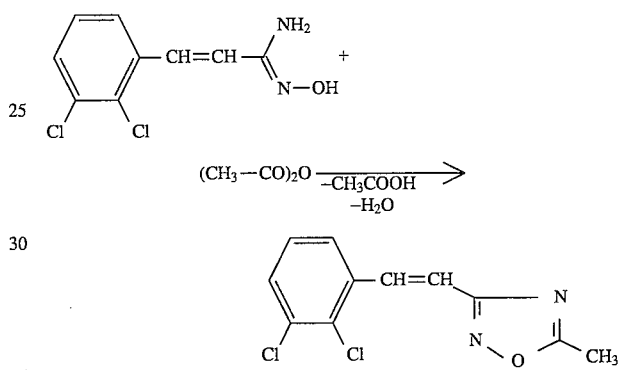

Preferred compounds of the formula (II) which are employed in process 2c) are those in which the radicals $R^2$, $R^3$ and $R^4$ have the preferred and particularly preferred meanings mentioned in the case of the compounds of the formula (I). The carboxylic anhydrides (V) furthermore to be used on starting substances for carrying out process 2c) according to the invention are generally defined. The carboxylic anhydrides of the formula (V) are generally known compounds of organic chemistry. The reaction is carried out and the reaction products are worked up and isolated by generally customary methods (cf. also Preparation Examples).

If, in process 2d), (E)-3-chloro-2-fluoro-cinnamamide oxime is employed as compound of the formula (II) and trichloroacetyl chloride as compound of the formula (VI), the process Can be described by the following equation:

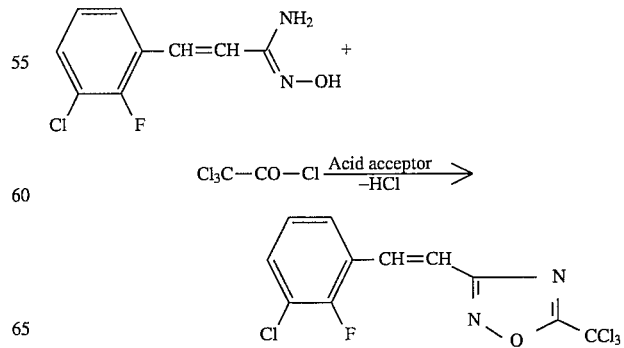

Preferred compounds of the formula (II) which are employed in process 2d) are those in which the radicals $R^2$, $R^3$ and $R^4$ have the preferred and particularly preferred meanings mentioned in the case of the compounds of the formula (I). The carboxylic acid chlorides (VI) which are furthermore to be used on starting substances for carrying out process 2d) according to the invention are generally defined. The carboxylic acid chlorides (VI) are generally known compounds of organic chemistry or can be prepared by methods known per se.

The reaction resembles the conventional Tiemann acylation synthesis and is preferably carried out using diluents.

Diluents which are used for carrying out process 2d) are the halogenohydrocarbons, in particular chlorohydrocarbons, which are mentioned in the case of process 2b).

Process 2d) according to the invention is carried out in the presence of a basic reaction auxiliary. As bases, bases which can be employed are all suitable acid-binding agents such as amines, in particular tertiary amines, and also alkali metal compounds and alkaline earth metal compounds. Examples of these which may be mentioned are the hydroxides, oxides and carbonates of lithium, sodium, potassium, magnesium, calcium and barium, furthermore other basic compounds such as trimethylamine, tribenzylamine, triisopropylamine, tributylamine, tribenzylamine, tricyclohexylamine, triamylamine, trihexylamine, N,N-dimethylaniline, N,N-dimethyltoluidine, N,N-dimethyl-p-aminopyridine, N-methyl-pyrrolidine, N-methyl-piperidine, N-methylimidazole, N-methylpyrrole, N-methyl-morpholine, N-methyl-hexamethyleneimine, pyridine, quinoline, α-picoline, β-picoline, isoquinoline, pyrimidine, acridine, N,N,N',N'-tetra-methylenediamine, N,N,N',N'-tetraethylenediamine, quinoxaline, N-propyl-diisopropylamine, N,N'-dimethylcyclohexylamine, 2,6-lutidine, 2,4-lutidine, triethylenediamine, diazabicyclooctane (DABCO), diazabicyclononene (DBN) or diazabicycloundecene (DBU).

Tertiary amines such as, for example, triethylamine or pyridine, are preferably used.

Process 2d) is carried out by combining compounds of the formula (II) with an excess of the compounds of the formula (VI) in one of the diluents mentioned and in the presence of a basic reaction auxiliary and, if appropriate, heating the mixture. The duration of the reaction is 1 to 6 hours. The reaction is carried out at temperatures between 0° C. and +200° C., preferably between +20° C. and +150° C. It is carried out under atmospheric pressure.

When the reaction is complete, the reaction mixture is filtered and concentrated in vacuo, and the residue which remains is purified in the customary manner by recrystallisation, distillation in vacuo, or column chromatography.

In the case of processes 2c) and 2d) according to the invention, it is possible for an O-acyl derivative of a compound of the formula (II) to be formed as an intermediate, which does not cyclise spontaneously. In such cases, the O-acyl compound mentioned, which is obtained as an intermediate, can be cyclised for example by refluxing, advantageously in suitable diluents, such as aromatic hydrocarbons.

The substituted 1,2,4-oxadiazole derivatives of the formula (I) which can be obtained with the aid of processes 2a), 2b), 2c) or 2d) according to the invention are generally obtained in the form of (E) isomers.

While having favourable toxicity to warm-blooded species, the active compounds are suitable for combating pathogenic endoparasites which occur in humans and in animal keeping and livestock breeding, in productive livestock, breeding animals, zoo animals, laboratory animals, experimental animal's and pets. In this context, they are active against all or individual stages of development of the pests and against resistant and normally-sensitive species. By combating the pathogenic endoparasites, it is intended to reduce disease, deaths and decreases in performance (for example in the production of meat, milk, wool, hides, eggs, honey etc.), so that more economical and simpler animal keeping is possible by using the active compounds. The pathogenic endoparasites include Cestodes, Trematodes, Nematodes and Acantocephalae, in particular:

From the order of the Pseudophyllidea, for example: Diphyllobothrium spp., Spirometra spp., Schistocephalus spp., Ligula spp., Bothridium spp., Diplogonoporus spp..

From the order of the Cyclophyllidea, for example: Mesocestoides spp., Anoplocephala spp., Paranoplocephala spp., Moniezia spp., Thisanosoma spp., Thysaniezia spp., Avitellina spp., Stilesia spp., Cittotaenia spp., Andyra spp., Bertiella spp., Taenia spp., Echinococcus spp., Hydatigera spp., Davainea spp., Raillietina spp., Hymenolepis spp., Echinolepis spp., Echinocotyle spp., Diorchis spp., Dipylidium spp., Joyeuxiella spp., Diplopylidium spp..

From the subclass of the Monogenea, for example: Gyrodactylus spp., Dactylogyrus spp., Polystoma spp..

From the subclass of the Digenea, for example: Diplostomum spp., Posthodiplostomum spp., Schistosoma spp., Trichobilharzia spp., Ornithobilharzia spp., Austrobilharzia spp., Gigantobilharzoia spp., Leucochloridiumspp., Brachylaima spp., Echinostoma spp., Echinoparyphium spp., Echinochasmus spp., Hypoderaeum spp., Fasciola spp., Fasciolides spp., Fasciolopsis spp., Cyclocoelumspp., Typhlocoelumspp., Paramphistomumspp., Calicophoron spp., Cotylophoron spp., Gigantocotyle spp., Fischoederius spp., Gastrothylacus spp., Notocotylus spp., Catatropis spp., Plagiorchis spp., Prosthogonimus spp., Dicrocoelium spp., Eurytrema spp., Troglotrema spp., Paragonimus spp., Collyriclum spp., Nanophyetus spp., Opisthorchis spp., Clonorchis spp. Metorchis spp., Heterophyes spp., Metagonimus spp..

From the order of the Enoplida, for example: Trichuris spp. , Capillaria spp., Trichomosoides spp., Trichinella spp..

From the order of the Rhabditia, for example: Micronema spp., Strongyloides spp..

From the order of the Strongylida, for example: Strongylus spp., Triodontophorus spp., Oesophagodontus spp., Trichonema spp., Gyalocephalus spp., Cylindropharynx spp., Poteriostomum spp., Cyclococercus spp., Cylicostephanus spp., Oesophagostomum spp., Chabertia spp., Stephanurus spp., Ancylostoma spp., Uncinaria spp., Bunostomum spp., Globocephalus spp., Syngamus spp., Cyathostoma spp., Metastrongylus spp., Dictyocaulus spp., Muellerius spp., Protostrongylusspp., Neostrongylus spp., Cystocaulus spp., Pneumostrongylus spp., Spicocaulus spp. , Elaphostrongylus spp. Parelaphostrongylus spp., Crenosoma spp., Paracrenosoma spp., Angiostrongylus spp., Aelurostrongylus spp., Filaroides spp., Parafilaroides spp., Trichostrongylus spp., Haemonchus spp., Ostertagia spp., Marshallagia spp., Cooperia spp., Nematodirus spp., Hyostrongylus spp., Obeliscoides spp., Amidostomum spp., Ollulanus spp..

From the order of the Oxyurida, for example: Oxyuris spp., Enterobius spp., Passalurus spp., Syphacia spp., Aspiduluris spp., Heterakis spp..

From the order of the Ascaridia, for example: Ascaris spp., Toxascaris spp., Toxocara spp., Parascaris spp., Anisakis spp., Ascaridia spp..

From the order of the Spirurida, for example: Gnathostoma spp., Physaloptera spp., Thelazia spp., Gongylonema spp., Habronema spp., Parabronema spp., Draschia spp., Dracunculus spp..

From the order of the Filariida, for example: Stephanofilaria spp., Parafilaria spp., Setaria spp., Loa spp., Dirofilaria spp., Litomosoides spp., Brugia spp., Wuchereria spp., Onchocerca spp..

From the order of the Gigantorhynchida, for example: Filicollis spp., Moniliformis spp., Macracanthorhynchus spp., Prosthenorchis spp.

The productive livestock and breeding animals include mammals such as, for example, cattle, horses, sheep, pigs, goats, camels, water buffaloes, donkeys, rabbits, fallow deer, reindeer, fur-bearing animals such as, for example, mink, chinchilla and racoon, birds such as, for example, chickens, geese, turkeys and ducks, freshwater and salt-water fish such as, for example, trout, carp and eels, reptiles, insects such as, for example, honey-bee and silkworm.

Laboratory animals and experimental animals include mice, rats, guinea pigs, golden hamsters, dogs and cats.

Pets include dogs and cats.

Administration can be effected prophylactically as well as therapeutically.

The active compounds are administered, directly or in the form of suitable preparations, enterally, parenterally, dermally, nasally, by treatment of the environment or With the aid of active-compound-containing shaped articles such as, for example, strips, plates, bands, collars, ear tags, limb bands, marking devices.

Enteral administration of the active compounds is effected, for example, orally, in the form of powders, tablets, capsules, pastes, drinks, granules, or solutions, suspensions and emulsions which can be administered orally, or boli, medicated feed or drinking water. Dermal administration is effected, for example, in the form of dipping, spraying or pouring-on and spotting-on. Parenteral administration is effected, for example, in the form of injection (intramuscularly, subcutaneously, intravenously, intraperitoneally) or by implants.

Suitable preparations are:

solutions such as solutions for injection, oral solutions, concentrates for oral administration after dilution, solutions for use on the skin or in body cavities, pour-on and spot-on formulations, gels;

emulsions and suspension for oral or dermal administration and for injection; semi-solid preparations;

formulations in which the active compound is incorporated in a cream base or in an oil-in-water or water-in-oil emulsion base;

solid preparations such as powders, premixes or concentrates, granules, pellets, tablets, boli, capsules; aerosols and inhalants, shaped articles containing active compound.

Solutions for injection are administered intravenously, intramuscularly and subcutaneously.

Solutions for injection are prepared by dissolving the active compound in a suitable solvent and, if appropriate, adding additives such as solubilisers, acids, bases, buffer salts, antioxidants and preservatives. The solutions are sterile-filtered and drawn off.

The following may be mentioned as solvents: physiologically acceptable solvents such as water, alcohols such as ethanol, butanol, benzyl alcohol, glycerol, propylene glycol, polyethylene glycols, N-methyl-pyrrolidone, and mixtures of these.

If appropriate, the active compounds can also be dissolved in physiologically acceptable vegetable or synthetic oils which are suitable for injection.

The following may be mentioned as solubilisers: solvents which enhance solution of the active compound in the main solvent or which prevent its precipitation. Examples are polyvinylpyrrolidone, polyoxyethylated castor oil, polyoxyethylated sorbitan esters.

Preservatives are: benzyl alcohol, trichlorobutanol, p-hydroxybenzoic esters, n-butanol.

Oral solutions are administered directly. Concentrates are administered orally after previously having been diluted to the administration concentration. Oral solutions and concentrates are prepared as described above in the case of the solutions for injection, it being possible to dispense with working under sterile conditions.

Solutions for use on the skin are applied dropwise, brushed on, rubbed in, splashed on or sprayed on. These solutions are prepared as described above in the case of solutions for injection.

It may be advantageous to add thickeners during the preparation. Thickeners are: inorganic thickeners such as bentonite, colloidal silica, aluminium monostearate, organic thickeners such as cellulose derivatives, polyvinyl alcohols and their copolymers, acrylates and methacrylates.

Gels are applied to, or brushed on, the skin, or introduced into body cavities. Gels are prepared by treating solutions which have been prepared as described in the case of the solutions for injection with such an amount of thickener that a clear substance of cream-like consistency is formed. Thickeners employed are the thickeners indicated further above.

Pour-on and spot-on formulations are poured onto, or splashed onto, limited areas of the skin, the active compound penetrating the skin and acting systemically.

Pour-on and spot-on formulations are prepared by dissolving, suspending or emulsifying the active compound in suitable solvents or solvent mixtures which are tolerated by the skin. If appropriate, other adjuvants such as colorants, resorption accelerators, antioxidants, light stabilisers, and tackifiers are added.

Solvents which may be mentioned are: water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol mono-methyl ether, diethylene glycol mono-butyl ether, ketones such as acetone, methyl ethyl ketone, aromatic and/or aliphatic hydrocarbons, vegetable or synthetic oils, DMF, dimethylacetamide, N-methyl-pyrrolidone, 2,2-dimethyl-4-oxy-methylene-1,3-dioxolane.

Colorants are all colorants which are permitted for use on animals and which can be dissolved or suspended.

Examples of resorption accelerators are DMSO, spreading oils such as isopropyl myristate, dipropylene glycol pelargonate, silicone oils, fatty acid esters, triglycerides, fatty alcohols.

Antioxidants are sulphites or metabisulphites such as potassium metabisulphite, ascorbic acid, butylhydroxytoluene, butylhydroxyanisole, tocopherol.

Examples of light stabilizers are novantisolic acid.

Examples of tackifiers are cellulose derivatives, starch derivatives, polyacrylates, natural polymers such as alginates, gelatine.

Emulsions can be administered orally, dermally or in the form of injections.

Emulsions are either of the water-in-oil type or of the oil-in-water type.

They are prepared by dissolving the active compound either in the hydrophobic or in the hydrophilic phase and homogenising this phase with the solvent of the other phase, with the aid of suitable emulsifiers and, if appropriate, other adjuvants such as colorants, resorption accelerators, preservatives, antioxidants, light stabilisers, viscosity-increasing substances.

The following may be mentioned as the hydrophobic phase (oils): paraffin oils, silicone oils, natural vegetable oils such as sesame seed oil, almond oil, castor oil, synthetic triglycerides such as caprylic/capric acid biglyceride, triglyceride mixture with vegetable fatty acids of chain length $C_{8-12}$ or with other specifically selected natural fatty acids, partial glyceride mixtures of saturated or unsaturated fatty acids which may also contain hydroxyl groups, and mono- and diglycerides of the $C_8/C_{10}$-fatty acids.

Fatty acid esters such as ethyl stearate, di-n-butyryl adipate, hexyl laurate, dipropylene glycol pelargonate, esters of a branched fatty acid of medium chain length with saturated fatty alcohols of chain length $C_{16}$–$C_{18}$, isopropyl myristate, isopropyl palmitate, caprylic/capric esters of saturated fatty alcohols of chain length $C_{12}$–$C_{18}$, isopropyl stearate, oleyl oleate, decyl oleate, ethyl oleate, ethyl lactate, waxy fatty acid esters such as artificial uropygial gland fat from ducks, dibutyl phthalate, diisopropyl adipate, ester mixtures related to the latter etc.

Fatty alcohols Such as isotridecyl alcohol, 2-octyldodecanol, cetylstearyl alcohol, oleyl alcohol.

Fatty acids such as, for example, oleic acid and its mixtures.

The following may be mentioned as hydrophilic phase: water, alcohols such as, for example, propylene glycol, glycerol, sorbitol and their mixtures.

The following may be mentioned as emulsifiers: non-ionic surfactants, for example polyoxyethylated castor oil, polyoxyethylated sorbitan monooleate, sorbitan monostearate, glycerol monostearate, polyoxyethyl stearate, alkylphenol polyglycol ethers;

ampholytic surfactants such as Di-Na N-lauryl-β-iminodipropionate or lecithin;

anionic surfactants, such as Na-lauryl sulphate, fatty alcohol ether sulphates, the monoethanolamine salt of mono/ dialkylpolyglycol ether orthophosphoric esters;

cationic surfactants such as cetyltrimethylammonium chloride.

The following may be mentioned as other adjuvants: viscosity-increasing substances and substances which stabilise the emulsion, such as carboxymethylcellulose, methylcellulose and other cellulose and starch derivatives, polyacrylates, alginates, gelatine, gum arabic, polyvinylpyrrolidone, polyvinyl alcohol, copolymers of methyl vinyl ether and maleic anhydride, polyethylene glycols, waxes, colloidal silica or mixtures of the substances mentioned.

Suspensions can be administered orally, dermally or in the form of injection. They are prepared by suspending the active compound in an excipient liquid if appropriate with the addition of further adjuvants such as wetting agents, colorants, resorption accelerators, preservatives, antioxidants and light stabilisers.

Excipient liquids which may be mentioned are all homogeneous solvents and solvent mixtures.

Wetting agents (dispersants) which may be mentioned are the surfactants indicated further above.

Further adjuvants which may be mentioned are those indicated further above.

Semi-solid preparations can be administered orally or dermally. They are only distinguished from the above-described suspensions and emulsions by their higher viscosity.

To prepare solid preparations, the active compound is mixed with suitable excipients, if appropriate with the addition of adjuvants, and the mixture is formulated as desired.

Excipients which may be mentioned are all physiologically acceptable solid inert substances. Suitable as such are inorganic and organic substances. Examples of inorganic substances are sodium chloride, carbonates such as calcium carbonate, hydrogen carbonates, aluminium oxides, silicas, clays, precipitated or colloidal silicon dioxide, and phosphates.

Examples of organic substances are sugars, cellulose, foods and animal feeds such as dried milk, animal meals, cereal meals and coarse cereal meals and starches.

Adjuvants are preservatives, antioxidants and colorants, which have already been indicated further above.

Other suitable adjuvants are the lubricants and gliding agents such as, for example, magnesium stearate, stearic acid, talc, bentonites, disintegrants such as starch or crosslinked polyvinylpyrrolidone, binders such as, for example, starch, gelatine or linear polyvinylpyrrolidone and also dry binders such as microcrystalline cellulose.

In the preparations, the active compounds can also be present in the form of a mixture with synergists or with other active compounds which act against pathogenic endoparasites. Examples of such active compounds are L-2,3,5,6-tetrahydro-6-phenylimidazothiazole, benzimidazole carbamates, praziquantel, pyrantel, febantel.

Ready-to-use preparations contain the active compound in concentrations of from 10 ppm to 20 per cent by weight, preferably of from 0.1 to 10 per cent by weight.

Preparations which are diluted prior to administration, contain the active compound in concentrations of from 0.5 to 90 per cent by weight, preferably of from 5 to 50 per cent by weight.

In general, it has proved advantageous to administer amounts of approximately 1 to approximately 100 mg of active compound per kg of body weight per day to achieve effective results.

Example A

In vivo nematode test

*Trichostrongylus colubriformis*/sheep

Sheep which have been experimentally infected with *Trichostrongylus colubriformis* were treated after the prepatency time of the parasite had elapsed. The active compounds were applied orally in gelatine capsules, in the form of pure active compound.

The degree of effectiveness is determined by quantitatively counting the worm eggs which have been excreted with the faeces before and after the treatment.

A complete standstill of egg excretion after the treatment means that the worms had been aborted or damaged to such an extent that they no longer produce eggs (*Dosis effectiva*).

Active compounds tested and effective dosage rates (*Dosis effectiva*) can be seen from the table which follows.

| Active compound Example No. | Dosis effectiva in mg/kg |
| --- | --- |
| 2 | 10 |
| 3 | 10 |
| 39 | 10 |
| 40 | 10 |
| 47 | 10 |

Example B

In vivo nematode test

*Haemonchus contortus*/sheep

Sheep which have been experimentally infected with *Haemonchus contortus* were treated after the prepatency time of the parasite had elapsed. The active compounds were applied orally in gelatine capsules, in the form of pure active compound.

The degree of effectiveness is determined by quantitatively counting the worm eggs which have been excreted with the faeces before and after the treatment.

A complete standstill of egg excretion after the treatment means that the worms had been aborted or damaged to such an extent that they no longer produce eggs (*Dosis effectiva*).

Active compounds tested and effective dosage rates (*Dosis effectiva*) can be seen from the table which follows:

| Active compound Example No. | Dosis effectiva in mg/kg |
|---|---|
| 3 | 10 |
| 39 | 10 |
| 47 | 10 |

PREPARATIVE EXAMPLES

Example 1

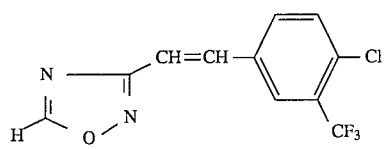

5.2 g (0.02 mol) of (E)-4-chloro-3-trifluoromethyl-cinnamamide oxime are introduced into 50 ml of triethyl orthoformate and 2 drops of boron trifluoride etherate are added at room temperature. The mixture is then stirred for 2 hours at reflux temperature and the entire batch is concentrated in vacuo. The residue is taken up in 100 ml of methylene chloride and washed in succession with 100 ml of 2N hydrochloric acid, saturated sodium carbonate solution and water. The organic phase is dried over sodium sulphate and the solvent is subsequently distilled off. 3.9 g (71.0 % of theory) of (E)-3-(4-chloro-3-trifluoromethyl-styryl)-1,2,4-oxadiazole are obtained.

M.p.: 85° to 87° C.

$^1$H NMR (CDCl$_3$, δ): 7.17; 7.71 (2d, =CH; J$_{H,H}$=16.3 Hz; E form); 7.24–8.70 (3 m, arom.); 9.68 (s, =CH) ppm The compounds of the formula (Ia, R$^1$=H) which are listed in Table 1 below can be prepared analogously.

TABLE 1

Examples of the compounds of the formula (Ia)

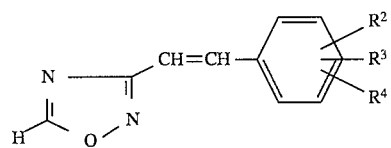

| Example No. | R$^2$ | R$^3$ | R$^4$ | Physical data |
|---|---|---|---|---|
| 2 | —H | 2-Cl | 3-Cl | m.p: 171–174° C. |
| 3 | —H | 2-F | 3-Cl | m.p.: 95–98° C. |
| 4 | —H | 2-CH$_3$ | 3-Cl | m.p.: 92–94° C. |
| 5 | —H | 3-CF$_3$ | 5-CF$_3$ | m.p.: 102–103° C. |
| 6 | —H | 2-NO$_2$ | 4-CF$_3$ | m.p.: 98–100° C. |
| 7 | —H | —H | 4-COOCH$_3$ | m.p.: 148–151° C. |
| 8 | —H | 3-Cl | 4-Cl | m.p.: 116–118° C. |
| 9 | —H | 2-Cl | 6-Cl | m.p.: 92–93° C. |
| 10 | —H | 2-F | 3-CF$_3$ | m.p.: 96–98° C. |
| 11 | —H | | 3,4-O—CF$_2$—O— | m.p.: 113–116° C. |
| 12 | —H | 2-F | 6-Cl | m.p.: 119–121° C. |
| 13 | —H | 2-Cl | 4-Cl | m.p.: 78–80° C. |
| 14 | —H | 2-F | 6-F | m.p.: 64–65° C. |
| 15 | —H | —H | 4-OCF$_3$ | m.p.: 74–75° C. |
| 16 | —H | —H | 4-SCF$_3$ | m.p.: 113–114° C. |
| 17 | —H | —H | 4-(O—CH$_2$—(2,6-diCl-phenyl)) | m.p.: 116–117° C. |
| 18 | —H | —H | 4-(O—CH$_2$—(4-Cl-phenyl)) | m.p.: 168–169° C. |
| 19 | —H | 2-Cl | 3-CF$_3$ | m.p.: 123–125° C. |
| 20 | —H | 3-F | 4-F | m.p.: 98–99° C. |
| 21 | —H | 2-F | 3-CH$_3$ | m.p.: 40° C. |
| 22 | —H | 3-CH$_3$ | 4-OCH$_3$ | m.p.: 91–92° C. |
| 23 | —H | 2-F | 3-F | m.p.: 104–105° C. |

TABLE 1-continued

Examples of the compounds of the formula (Ia)

| Example No. | R² | R³ | R⁴ | Physical data |
|---|---|---|---|---|
| 24 | —H | | 3,4-O—CH₂—O— | m.p.: 147–150° C. |
| 25 | —H | | 3,4-O—(CH₂)₂—O— | m.p.: 80° C. |
| 26 | —H | 2-CH₃ | 4-CH₃ | m.p.: 73–74° C. |
| 27 | —H | 2-OCH₃ | 3-OCH₃ | m.p.: 55–57° C. |
| 28 | —H | 3-Cl | 4-OCF₂CHCF₃ <br> \| <br> F | m.p.: 31–34° C. |
| 29 | —H | 3-Cl | 5-Cl | m.p.: 144–145° C. |
| 30 | —H | 3-Cl | 4-CF₃ | m.p.: 99–100° C. |
| 31 | —H | 3-Cl | 4-OCF₃ | m.p.: 57–58° C. |
| 32 | —H | 4-F | 3-CF₃ | m.p.: 78–79° C. |
| 33 | —H | 4-F | 3-Br | m.p.: 123–125° C. |
| 34 | —H | 3-Br | 4-OCH₃ | m.p.: 137–138° C. |
| 35 | —H | —H | 3-SCF₃ | m.p.: 89° C. |
| 36 | —H | — | 3-(O—⟨phenyl-CF₃⟩) | m.p.: 49–50° C. |
| 37 | —H | 3-Cl | 4-F | m.p.: 136–138° C. |

Example 38

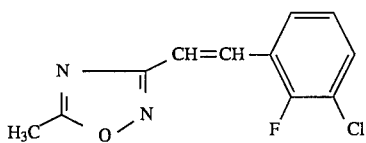

6.4 g (0.03 mol) of (E)-3-chloro-2-fluoro-cinnamamide oxime are introduced into 50 ml of acetic anhydride and the mixture is stirred for 2 hours at reflux temperature. The entire batch is subsequently concentrated in vacuo, the residue is stirred with sodiumcarbonate solution and the mixture is extracted with methylene chloride. The organic phase is dried over sodium sulphate and the solvent is distilled off. 5.1 g (75.6 % of theory) of (E)-3-(3-chloro-2-fluoro-styryl)-5-methyl-1,2,4-oxadiazole are obtained.

M.p.: 95° to 98° C.

¹H NMR (CDCl₃, δ): 2.60 (s, —CH₃ ); 7.16; 7.76 ( 2 d, =CH; $J_{H,H}$=16.5 Hz; E form); 7.09–7.51 (m, arom.) ppm The compounds of the formula (Ib, R¹—Me) which are listed in Table 2 below can be prepared analogously.

TABLE 2

Examples of the compounds of the formula (Ib)

| Example No. | R² | R³ | R⁴ | Physical data |
|---|---|---|---|---|
| 39 | —H | —H | 4-OCH₃ | m.p.: 109–110° C. |
| 40 | —H | 2-Cl | 3-Cl | m.p. 175–179° C. |
| 41 | —H | 2-CH₃ | 3-Cl | m.p.: 107–108° C. |
| 42 | —H | 3-CF₃ | 5-CF₃ | m.p.: 116–117° C. |
| 43 | —H | —H | 4-COOCH₃ | m.p.: 146–148° C. |
| 44 | —H | 3-F | 4-F | m.p.: 120–121° C. |

TABLE 2-continued

Examples of the compounds of the formula (Ib)

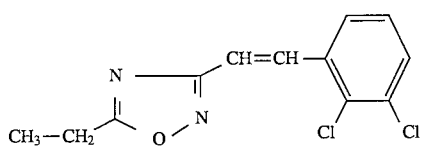

| Example No. | R² | R³ | R⁴ | Physical data |
|---|---|---|---|---|
| 45 | — | —H | 4-(O—CH₂—⟨phenyl⟩—OCH₃) | m.p.: 159–160° C. |
| 46 | —H | 2-F | 3-F | m.p.: 115–116° C. |

Example 47

7.0 g (0.03 mol) of (E)-2,3-dichloro-cinnamamide oxide are introduced into 7 ml of propionic anhydride and the mixture is stirred for 2 hours at reflux temperature. The entire batch is subsequently concentrated in vacuo, the residue is stirred with sodium carbonate solution and the mixture is extracted with methylene chloride. The organic phase is dried over sodium sulphate and the solvent is distilled off. 4.7 g (58.2 % of theory) of (E)-3-(2,3-dichloro-styryl)-5-ethyl-ethyl-1,2,4-oxadiazole are obtained.

M.p.: 107° to 109° C.

¹H NMR (CDCl₃, δ): 1.44 (t, —CH₃; $J_{H,H}$=7.6 Hz); 2.95 (q, —CH₂—; $J_{H,H}$=7.6 Hz); 7.02; 8.07 (2d, =CH; $J_{H,H}$=16.0 Hz); 7.21–7.59 (3 m, arom.) ppm The compounds of the formula (Ic, R¹=—Et) which are listed in Table 3 below can be prepared analogously.

Example 50

12.7 g (0.07 mol) of trichloroacetyl chloride are added dropwise to a suspension of 6.4 g (0.03 mol) of (E)-3-chloro-2-fluoro-cinnamamide oxime in 90 ml of chloroform and 6 ml (0.07 mol) of dry pyridine. During this process the temperature of the reaction mixture rises slightly. Stirring is subsequently continued for 1 hour, and the pyridine hydrochloride which separates out in this process is filtered off and washed with chloroform. The filtrate is concentrated in vacuo and the solid which remains is recrystallised. 5.0 g (48.7 % of theory) of (E)-3-(3-chloro-2-fluoro-styryl)-5-trichloromethyl-1,2,4-oxadiazole are obtained.

M.p.: 37° to 38° C.

¹H NMR (CDCl₃, δ): 7.12–7.52 (m, arom. +=CH); 7.87 (d, =CH; $J_{H,H}$=16.0 Hz) ppm The compounds of the formula (Id, R¹=—CCl₃) which are listed in Table 4 below can be prepared analogously.

TABLE 3

Examples of the compounds of the formula (Ic)

| Example No. | R² | R³ | R⁴ | Physical data |
|---|---|---|---|---|
| 48 | —H | —H | 4-OCH₃ | m.p.: 38–40° C. |
| 49 | —H | 2-Cl | 4-COOCH₃ | m.p.: 79–80° C. |

TABLE 4

Examples of the compounds of the formula (Id)

| Example No. | R² | R³ | R⁴ | Physical data |
|---|---|---|---|---|
| 51 | —H | —H | 4-OCH₃ | m.p.: 126–129° C. |
| 52 | —H | 3-CF₃ | 5-CF₃ | m.p.: 86–87° C. |

Example 53

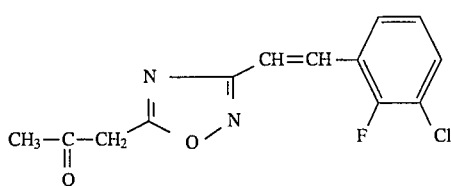

4.3 g (0.02 mol) of (E)-3-chloro-2-fluoro-cinnamamide oxime were introduced into 85 ml of toluene, 16.9 g (0.13 mol) of ethyl acetate were added and the mixture was stirred at reflux temperature until the reaction was complete (45 hours). After this the entire batch is concentrated in vacuo and the residue which remains is recrystallised.

4.3 g (76.6 % of theory) of (E)-3-(3-chloro-2-fluorostyryl)-5-(2-oxopropyl)-1,2,4-oxadiazole is obtained as a keto/enol tautomer mixture (81:19).

M.p.: 75° to 77° C.

$^1$H NMR (CDCl$_3$, δ): 2.15; 2.36 (2s, —CH$_3$); 4.09 (s, —CH$_2$—); 5.56 (s, =CH); 7.18; 7.7; 7.78 (3d, =CH, J$_{H,H}$= 16.3 Hz; E form); 7.10–7.51 (m, arom. +=CH); 11.40 (s, —OH) ppm The compounds of the formula (Ie, R$^1$=—CH$_2$COCH$_3$) which are listed in Table 5 below can be prepared analogously.

TABLE 5

Examples of the compounds of the formula (Ie)

| Example No. | R$^2$ | R$^3$ | R$^4$ | Physical data |
|---|---|---|---|---|
| 54 | —H | 2-Cl | 3-Cl | m.p.: 110–112° C. |
| 55 | —H | 3-CF$_3$ | 5-CF$_3$ | m.p.: 122–123° C. |

TABLE 5-continued

Examples of the compounds of the formula (Ie)

| Example No. | R$^2$ | R$^3$ | R$^4$ | Physical data |
|---|---|---|---|---|
| 56 | —H | 2-CH$_3$ | 3-Cl | m.p.: 96–97° C. |
| 57 | —H | —H | 4-OCH$_3$ | m.p.: 90–92° C. |

Starting substances of the formula (II)

Example (II-1)

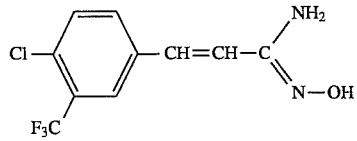

12.1 g (0.05 mol) of 4-chloro-3-trifluoromethyl-cinnamonitrile are added to a solution of 7.2 g (0.10 mol) of hydroxylamine hydrochloride, 7.3 g (0.10 mol) of sodium carbonate in 100 ml of water, and 100 ml of ethanol. The mixture is refluxed until the reaction is complete (24 hours) and the entire batch is subsequently stirred into 250. ml of water. The solid which separates out during this process is filtered off with suction, washed with a little water and dried. 5.3 g (39.3 % of theory) of (E)-4-chloro-3-trifluoromethyl-cinnamamide oxide are obtained.

M.p.: 135° to 137° C.

$^1$H NMR (CDCl$_3$, δ): 5.64 (br s, —NH$_2$); 6.60; 7.15 (2d, =CH; J$_{H,H}$=16.5 HZ; E form); 7.68–10.00 (m, arom.); 11.89 (s, —OH ) ppm The compounds of the formula (II) listed in Table 6 below can be prepared analogously.

TABLE 6

Starting substances of the formula (II)

| Example No. | R$^2$ | R$^3$ | R$^4$ | Physical data |
|---|---|---|---|---|
| II-2 | —H | 2-F | 3-CF$_3$ | 5.75; 9.97 a) |
| II-3 | —H | 3-Cl | 4-Cl | 5.60; 9.92 a) |
| II-4 | —H | 2-Cl | 6-F | 5.74; 9.93 a) |
| II-5 | —H | 2-F | 6-F | m.p.: 165–166° C. |
| II-6 | —H | —H | 4-OCF$_3$ | 5.63; 9.84 a) |
| II-7 | —H | —H | 4-SCF$_3$ | 5.68; 9.94 a) |
| II-8 | —H | 2-Cl | 3-CF$_3$ | 4.93; 8.62 b) |
| II-9 | —H | 3-CH$_3$ | 4-OCH$_3$ | 5.55; 9.66 a) |
| II-10 | —H | | 3,4-O—CF$_2$—O— | 5.58; 9.00 E-form a) 5.33; 11.52 Z-form a) |
| II-11 | —H | | 3,4-O—(CH$_2$)$_2$—O— | 5.52; 9.65 a) |

TABLE 6-continued

Starting substances of the formula (II)

| Example No. | R² | R³ | R⁴ | Physical data |
|---|---|---|---|---|
| II-12 | —H | —H | 4-(O—CH₂—⌬—OCH₃) | 5.54; 9.64 a) | a) ¹H NMR(DMSO d₆, δ, ppm);
b) ¹H NMR(CDCl₃, δ, ppm); in each case singlets (broad) for

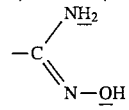

Example for the preparation of the substituted cinnamonitriles employed as precursors (cf., for example, Foucaud et el. Synthesis (1979), pp. 884 to 885):

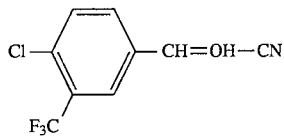

A solution of 10.6 g (0.06 mol) of diethyl cyanomethylphosphonate and 12.5 g (0.06 mol) of 4-chloro-3-trifluoromethyl-benzeldehyde in 65 ml of tetrahydrofuran is added dropwise to a suspension of 6.7 g (0.12 mol) of pulverulent potassium hydroxide in 185 ml of tetrahydrofuran. During this process the temperature of the reaction mixture rises slightly. Stirring is subsequently continued at room temperature for 20 minutes, and the solid which separates out in this process is filtered off and washed with tetrahydrofuran. The filtrate is concentrated in vacuo and the residue which remains is dried. 12.1 g (87.0 % of theory) of 4-chloro-3-trifluoromethyl-cinnamonitrile are obtained in the form of an E/Z isomer mixture.

M.p.: 89°–92° C.

¹H NMR (CDCl₃, δ): 5.60; 7.13 (2d, =CH, J$_{H,H}$12 Hz; Z form); 5.96; 7.38 (2d, =CH, J$_{H,H}$=16.5 Hz; E form); 7.57–8.07 ( m, arom.) ppm The compounds listed in Table 7 below can be prepared analogously.

TABLE 7

NC—CH=CH—⌬(R², R³, R³)

| Example No. | R² | R³ | R⁴ | Physical data |
|---|---|---|---|---|
| a | —H | 2-F | 3-CF₃ | 6.11; 7.53 E-form a) |
|   |    |     |       | 5.71; 7.45 Z-form |
| b | —H | 3-Cl | 4-Cl | 5.89; 7.30 E-form a) |
| c | —H | 2-Cl | 6-F | 5.89; 7.75 E-form a) |
|   |    |      |     | 5.62; Z-form |
| d | —H | 2-F | 6-F | 6.25; 7.46 E-form a) |
|   |    |     |     | 5.80; 7.14 Z-form |
| e | —H | —H | 4-OCF₃ | 5.87; 7.39 E-form a) |
|   |    |    |        | 5.51; 7.13 |
| f | —H | —H | 4-SCF₃ | 5.99; 7.44 E-form a) |
| g | —H | 2-Cl | 3-CF₃ | 5.95; 7.91 E-form a) |
|   |    |      |       | 5.74; 7.61 Z-form |
| h | —H | 3-CH₃ | 4-OCH₃ | 5.70; 7.30 E-form a) |
|   |    |       |        | 5.25; 7.00 Z-form |
| i | —H | 3.4-O—CF₂—O— | | 5.81; 7.35 E-form a) |
|   |    |              | | 5.47; Z-form |
| j | —H | 3.4-O—(CH₂)₂—O— | | 5.69; 7.28 E-form a) |
|   |    |                 | | 5.29; Z-form |

TABLE 7-continued

NC—CH=CH—[phenyl with R², R³, R³]

| Example No. | R² | R³ | R⁴ | Physical data |
|---|---|---|---|---|
| k | —H | —H | 4-(O—CH₂—[phenyl]—OCH₃) | 5.71; E-form a) | a) $^1$H NMR (CDCl$_3$, δ, ppm); in each case doublets ($J_{H,H}$ = 16.5 Hz; E form) and ($J_{H,H}$ = 12.0 Hz; Z form) for —CH=CH—

We claim:

1. A substituted 1,2,4-oxadiazole derivative or its enantiomer selected from the group consisting of

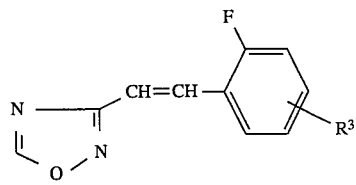
(A)

in which

R³ is 3—Cl, 3-methyl or 6—Cl,

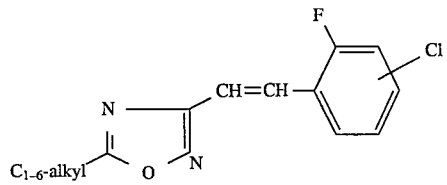
(B)

and (C) [structure with CH=CH linking oxadiazole (R¹) to benzodioxole bearing R²]

in which

R¹ is hydrogen, C$_{1-6}$-alkyl optionally substituted by halogen, or C$_{3-6}$ cycloalkyl, and R² is hydrogen, C$_{1-6}$-alkyl, NO$_2$, halogen, C$_{1-6}$-alkoxy or C$_{1-6}$-thioalkyl.

2. A substituted 1,2,4-oxadiazole derivative or its enantiomer according to claim 1 of the formula (A).

3. A substituted 1,2,4-oxadiazole derivative or its enantiomer according to claim 1 of the formula (B).

4. A substituted 1,2,4-oxadiazole derivative or its enantiomer according to claim 1 of the formula (c).

* * * * *

UNITED STATES PATENT AND TRADEMARK OFFICE
CERTIFICATE OF CORRECTION

PATENT NO. : 5,585,493
DATED : December 17, 1996
INVENTOR(S) : Jeschke, et al.

It is certified that error appears in the above-indentified patent and that said Letters Patent is hereby corrected as shown below:

Title Page    FOREIGN PATENT DOCUMENTS: Insert
-- 1228142 4/1971 United Kingdom --

Signed and Sealed this

Twenty-second Day of July, 1997

Attest:

BRUCE LEHMAN

*Attesting Officer*    *Commissioner of Patents and Trademarks*